(12) United States Patent
Zahner

(10) Patent No.: US 11,690,545 B2
(45) Date of Patent: Jul. 4, 2023

(54) SYSTEMS AND METHODS FOR MIXING DRAWN FLUIDS

(71) Applicant: The Board of Regents of the University of Texas System, Austin, TX (US)

(72) Inventor: Christopher John Zahner, League City, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 1036 days.

(21) Appl. No.: 16/357,990

(22) Filed: Mar. 19, 2019

(65) Prior Publication Data

US 2019/0282151 A1    Sep. 19, 2019

Related U.S. Application Data

(60) Provisional application No. 62/644,678, filed on Mar. 19, 2018.

(51) Int. Cl.
*A61B 5/15*    (2006.01)
*B01F 13/00*    (2006.01)
*B01F 11/00*    (2006.01)
*B01L 3/00*    (2006.01)
*A61J 1/05*    (2006.01)
(Continued)

(52) U.S. Cl.
CPC .. *A61B 5/150755* (2013.01); *A61B 5/150022* (2013.01); *A61B 5/150206* (2013.01); *A61B 5/150343* (2013.01); *A61J 1/05* (2013.01); *B01F 31/60* (2022.01);
(Continued)

(58) Field of Classification Search
CPC ...... B01F 2101/23; B01F 31/60; B01F 29/30; B01F 31/10; B01F 31/201; B01F 31/265; B01F 33/3017; B01F 33/50111; B01F 35/3202; B01F 35/3204; A61J 1/05; B01L 3/00; B01L 3/5082; B01L 9/06;
(Continued)

(56) References Cited

U.S. PATENT DOCUMENTS 3,633,566 A * 1/1972 Grabhorn ......... A61B 5/150351
604/903
4,278,437 A * 7/1981 Haggar ............... B01L 3/5082
422/547
(Continued)

FOREIGN PATENT DOCUMENTS

CN         105903383 A *  8/2016   ......... B01F 15/0441
FR           2859285 A1 *  3/2005   ......... B01F 11/0002
WO    WO-2014190998 A1 * 12/2014   ......... B01F 11/0022

OTHER PUBLICATIONS

Google machine translation for "CN-105903383-A" (Year: 2016).*
(Continued)

*Primary Examiner* — Elizabeth Insler
(74) *Attorney, Agent, or Firm* — Thomas Horstemeyer, LLP

(57) ABSTRACT

In one embodiment, a mixing device includes a sleeve that forms an inner space configured to receive a sample container, a housing associated with the sleeve, a mixing element contained within the housing that is configured to mix liquid contained within the sample container, and an activation element configured to activate the mixing element when the activation element is triggered.

5 Claims, 6 Drawing Sheets

(51) Int. Cl.
　　　*B01F 31/60* 　　　(2022.01)
　　　*B01F 33/301* 　　(2022.01)
　　　*B01F 101/23* 　　　(2022.01)

(52) U.S. Cl.
　　　CPC ............ *B01F 33/3017* (2022.01); *B01L 3/00* (2013.01); *B01F 2101/23* (2022.01)

(58) Field of Classification Search
　　　CPC ........ A61B 5/150022; A61B 5/150206; A61B 5/150343; A61B 5/150755
　　　See application file for complete search history.

(56) References Cited

U.S. PATENT DOCUMENTS

| | | | | |
|---|---|---|---|---|
| 5,399,013 | A | * | 3/1995 | Sawyer ................... B01F 31/26 366/110 |
| 5,971,599 | A | * | 10/1999 | Bothers ................... B01F 31/24 366/110 |
| 8,096,958 | B2 | | 1/2012 | Sarstedt |
| 9,211,513 | B1 | * | 12/2015 | Korpela .............. B01F 33/5011 |
| 2008/0169043 | A1 | * | 7/2008 | Osborne ............... B01F 35/422 141/1 |

OTHER PUBLICATIONS

Google machine translation for "FR-2859285-A1" (Year: 2005).*
Shat, et al., "Neonatal capillary bold sampling", Acutecaretesting.org; Jul. 2005.
McCoy, et al. "Reducing CBC clotting rates in the neonatal patient care areas", MBJ Quality; May 25, 2016.
Peng, et al., "Comparison of performances of five capillary blood collection tubes", International Journal of Laboratory Hematology; Feb. 25, 2014.
Instructables, The World's Biggest Show and Tell; Mixer for Test Tubes; One-lightbulb; Feb. 18, 2008.
Innovac Quick Draw, "Quality Micro Samples from Your Difficult to Draw Patients", Innovative Med Tech, www.innovativemedtech.com, 2008.

* cited by examiner

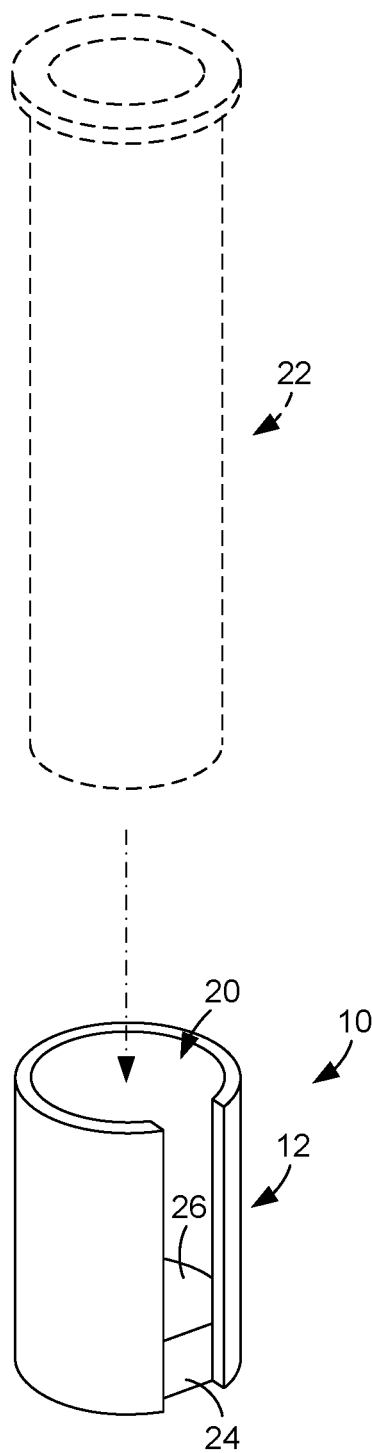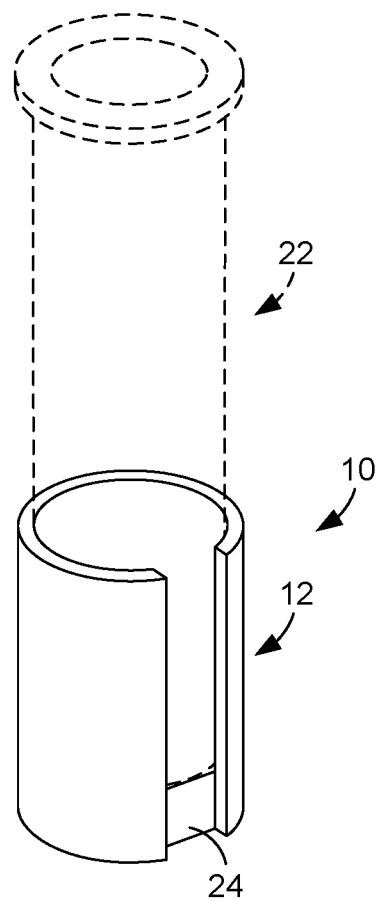
FIG. 2A  FIG. 2B

SYSTEMS AND METHODS FOR MIXING DRAWN FLUIDS

CROSS-REFERENCE TO RELATED APPLICATION

This application claims priority to U.S. Provisional Application Ser. No. 62/644,678, filed Mar. 19, 2018, which is hereby incorporated by reference herein in its entirety.

BACKGROUND

Currently, many neonatal intensive care unit (NICU) patients have their blood drawn using a heel-stick lancet. In many of the cases (roughly 5-20% nationwide), the sample comes to the lab either clotted or hemolyzed, rendering the sample deteriorated or useless. In such cases, testing for the patient is either skipped for the day, resulting in lost medical knowledge for the clinical team, or an additional sample is taken, which results in additional blood loss and pain for the patient. Wasted samples are a concern for NICUs because of the fragility of the patient population and impact of their blood loss.

In the case of clotted samples, most wastage could have been avoided if the sample had been properly handled while it was being drawn. Several minutes may be required to fill a sample tube with blood during a heel-stick procedure as the blood normally flows slowly from the patient. To avoid clotting, a cap is supposed to be applied to the tube midway through the sample collection and the tube inverted so that an anticoagulant contained within the tube will be mixed into the sample, which prevents the blood from clotting. However, as performing a heel-stick procedure is difficult and often involves a very small and frail crying baby, it can be difficult to remember to perform this mixing during collection.

In addition to NICUs, there are other situations in which sample mixing at the time of collection would be useful, such as for veterinary samples, research applications in which reagent mixing and sample wastage is costly, practitioner training, and the like.

From the foregoing discussion, it can be appreciated that it would be desirable to have a system and method for automatically mixing drawn fluids as it is collected.

BRIEF DESCRIPTION OF THE DRAWINGS

The present disclosure may be better understood with reference to the following figures. Matching reference numerals designate corresponding parts throughout the figures, which are not necessarily drawn to scale.

FIGS. 2A and 2B are perspective views illustrating use of the mixing device of FIG. 1 with a sample container.

DETAILED DESCRIPTION

As described above, it would be desirable to have a system and method for automatically mixing drawn fluids as it is collected. Disclosed herein are examples of such systems and methods. In some embodiments, the systems and methods comprise a mixing device that can either be associated with or integrated with a sample container. When activated, the mixing device gently mixes the drawn fluid within the container. In embodiments in which the drawn fluid comprises blood and the sample container contains an anticoagulant, the blood is mixed with the anticoagulant so that the blood will not clot. In some embodiments, the mixing device comprises a sleeve that is configured to receive the sample container and automatically activates a mixing element of the device that is configured to mix the fluid within the container.

In the following disclosure, various specific embodiments are described. It is to be understood that those embodiments are example implementations of the disclosed inventions and that alternative embodiments are possible. Such embodiments include hybrid embodiments in which aspects of different embodiments are combined together. All such embodiments are intended to fall within the scope of this disclosure.

Figure 1:
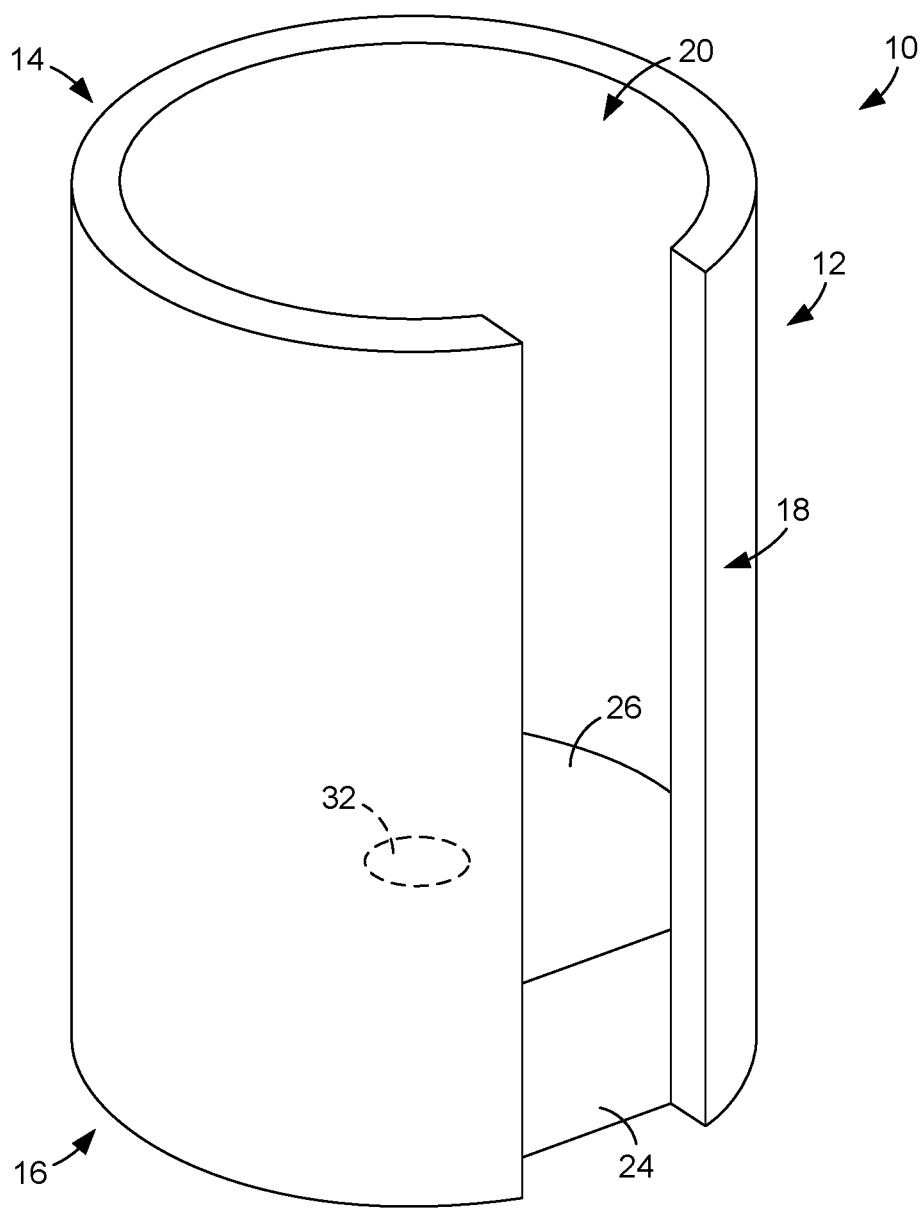
FIG. 1 is a perspective view of a first embodiment of a mixing device configured to mix drawn fluid collected in a sample container.

FIG. 1 illustrates a first embodiment of a mixing device 10. As shown in this figure, the mixing device 10 comprises a generally cylindrical sleeve 12 having a top end 14 and a bottom end 16. In some embodiments, the sleeve 12 includes an elongated slot 18 that extends along the entire or nearly the entire length of the sleeve from the top end 14 toward the bottom end 16. The sleeve 12 defines a generally cylindrical inner space 20 that, as illustrated in FIGS. 2A and 2B, is configured to receive a sample container 22. As shown in these figures, the sample container 22 can comprise a generally cylindrical tube and can be slid into the inner space 20. Provided at the bottom of the inner space 20 near the bottom end 16 of the sleeve 12 is a housing 24 that forms an inner bottom surface 26 of the inner space. In addition, the housing 24 defines a sealed inner compartment that contains at least a mixing element (see FIG. 3) that is configured to mix liquid contained within the sample container 22.

Figure 3:
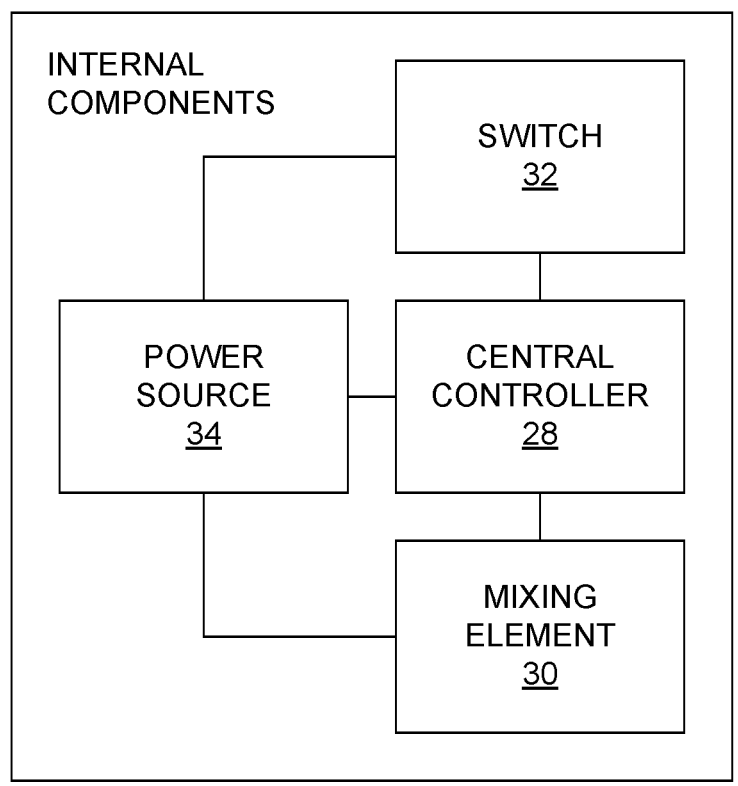
FIG. 3 is a block diagram of an embodiment of internal components of the mixing device of FIG. 1.

FIG. 3 is a block diagram that identifies example internal components of the mixing device 10 that can be at least partially contained within the housing 24. In the illustrated example, these components include a central controller 28 that controls the overall operation of the mixing device 10, a mixing element 30 that is used to mix drawn fluid contained within the sample container 22, a switch 32 (i.e., activation element) that is used to activate the mixing element, and a power source 34, such as a rechargeable battery or capacitor, that supplies power to the other components.

By way of example, the mixing element 30 can comprise at least one vibration motor that generates and transmits vibrations to the sample container 22 that mix the collected liquid. In situations in which the liquid is blood and the container 22 includes an anticoagulant, such as ethylenediamine tetraacetic acid (EDTA), this mixing can prevent clotting of the blood. The switch 32 can comprise an activation switch that is automatically triggered at some point during the fluid collection procedure. For example, as depicted in FIG. 1, a switch 32 can be incorporated into the inner bottom surface 26 of the inner space 20 so that, when the sample container 22 is fully received within the sleeve 12, the switch is triggered and the mixing element 30 is activated.

As expressed above, it can take a long time to collect blood samples from certain patients and, as a consequence, the drawn blood samples can clot, rendering the sample useless. Such an outcome can be avoided, however, when the mixing device 10 is used. In such a case, the sample container 22 is received within the inner space 20 of the sleeve 12 until it abuts the housing 24 provided at the bottom end of the space (see FIG. 2B). When such abutment occurs, the activation switch 32 is triggered so as to automatically activate the mixing element 30. In cases in which the mixing element includes a vibration motor, the motor can operate at a speed of approximately 5,000 to 10,000 rpm. The vibrations created by the vibration motor cause gentle agitation of the fluid sample that has been and is being collected in the sample container 22 and mixing of the fluid sample with the anticoagulant within the container (when present). In the case in which the liquid is blood and an anticoagulant is present, this agitation and mixing inhibits clotting and, therefore, ensures the sample is viable for laboratory testing. Notably, because the mixing element 30 is automatically activated, the medical practitioner (e.g., nurse) need not remember to perform any manual mixing, as is currently recommended but often forgotten. In some embodiments, a timer integrated into the central controller 28 can automatically shut off operation of the mixing element 30 after the expiration of a predetermined period of time (e.g., 30-60 seconds) if the sample container 22 is not removed before such expiration.

It is noted that, when the mixing element 30 is a vibration motor, the motor can be placed in various orientations. For example, the vibration motor can be orientated so as to generate vibrations that propagate in a direction that is parallel or perpendicular to the longitudinal axis of the sleeve 12 and, therefore, the sample container 22. When two vibration motors are provided, one can be orientated so as to generate vibrations in a direction that is parallel to the longitudinal axis of the sleeve 12 and the other can be orientated so as to generate vibrations in a direction that is perpendicular to the longitudinal axis of the sleeve 12. In such a case, one or both of the vibration motors 32 can be activated when the sample container 22 is received by the sleeve 12. In some embodiments, the user can select which vibration motor to activate with a further switch 32 (not shown). In other embodiments, the mixing device 10 further includes an orientation sensor (not shown) and the vibration motor that is activated depends upon the sensed orientation of the mixing device. It is also noted that the vibration motor(s) can be operated at various speeds. In some embodiments, the mixing device 10 further includes a variable speed controller (not shown) that can vary the motor speed either responsive to a user input or in accordance with the programming of the central controller 28 and/or a sensed condition.

Figure 4:
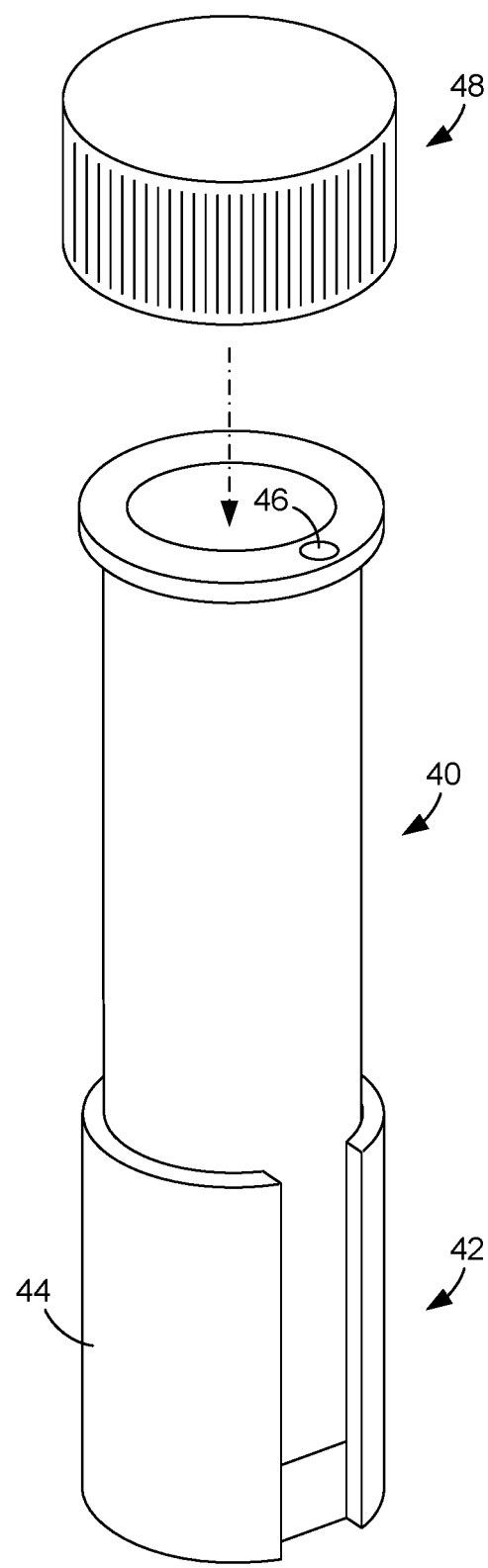
FIG. 4 is a perspective view of a second embodiment of a mixing device configured to mix drawn fluid collected in a sample container.

As is apparent from the above disclosure, the mixing device 10 is independent of the sample container 22. In other embodiments, however, the mixing device 10 can be integrated with a sample container. FIG. 4 illustrates an example of this. As shown in this figure, a sample container 40 includes an integrated mixing device 42. As in the previous embodiment, the mixing device 42 comprises a generally cylindrical sleeve 44 that surrounds the generally cylindrical body of the sample container 40. As the mixing device 42 is integrated with the sample container 40, the mixing element within the mixing device (which can be similar to that of the previous embodiment) is not activated upon receiving the sample container. Instead, the mixing element can be activated by an activation switch 46 provided at the top end of the sample container 40. In such a case, removing a cap 48 of the sample container 40 trips the activation switch 46 (which senses absence of the cap) and this causes activation of the mixing element. As before, the mixing element is automatically activated, and the medical practitioner need not remember to perform any manual mixing.

Figure 5:
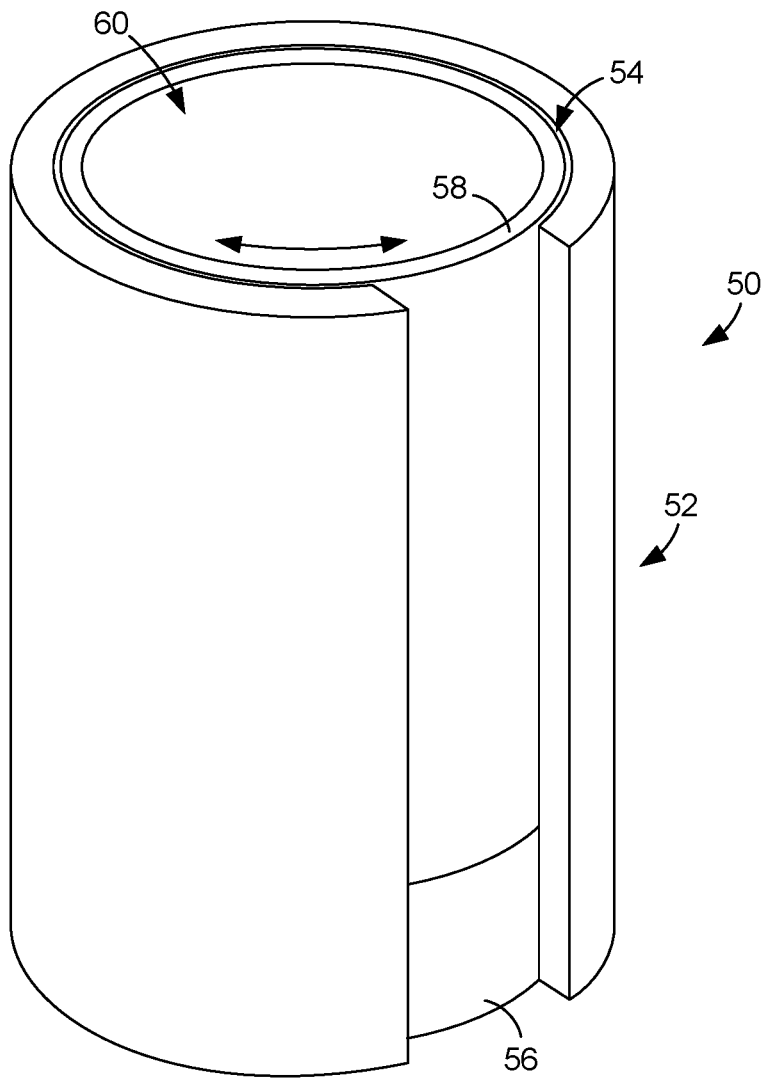
FIG. 5 is a perspective view of a third embodiment of a mixing device configured to mix drawn fluid collected in a sample container.

While the mixing element has been described above as comprising one or more vibration motors, it is noted that other types of mixing elements can used. FIG. 5 illustrates a mixing device 50 that utilizes a rotary motion to achieve mixing. As shown in FIG. 5, the mixing device 50 is similar in several ways to the mixing device 10 shown in FIG. 1. Accordingly, the mixing device 50 comprises a generally cylindrical sleeve 52 that defines a generally cylindrical inner space 54 and a housing 56 that defines a sealed inner compartment that at least contains a mixing element that is configured to mix liquid contained within the sample container 22. In this embodiment, however, provided within the sleeve 52 is a further inner sleeve 58 having its own generally cylindrical inner space 60 that is configured to receive the sample container 22. The inner sleeve 58 is configured to rotate or spin about its longitudinal axis relative to the outer cylindrical sleeve 52 for purposes of mixing the liquid contained in the sample container 22. In some embodiments, the inner sleeve 58 is supported within the outer sleeve 52 by a bearing that enables the inner sleeve to freely rotate.

Figure 6:
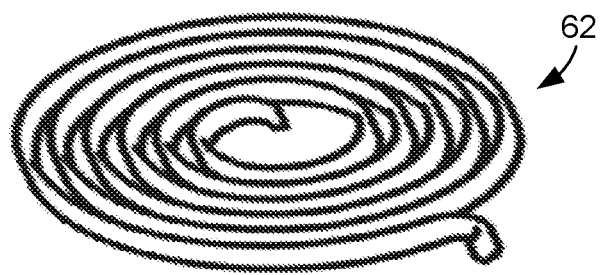
FIG. 6 is a perspective view of a spiral torsion spring that can be used in the mixing device of FIG. 5.

The mixing element provided in the housing 56 drives the inner sleeve 58. This mixing element can comprise an electrically powered element, such as an electric motor, or a passive element, such as a coiled spiral torsion spring, that is released and enabled to uncoil, thereby providing rotary motion to the inner sleeve 58. An example of such a spiral torsion spring 62 is illustrated in FIG. 6. In embodiments in which the mixing element is a spring or other passive element, no power is required to achieve mixing of the fluid, thereby simplifying the device design and reducing its cost of fabrication. Various mechanisms can be used to release the spring or other passive element. For example, a passive activation element, such as a pin, can be provided in the housing 56 that maintains the inner sleeve 58 and spring in their initial orientations (the spring tightly coiled) and insertion of the sample container 22 into the inner sleeve 58 displaces the activation element in a manner in which the inner sleeve and spring are released, thereby causing the spring to spin the inner sleeve and, therefore, the sample container. In such a case, mixing is automated even though no electrical power is used. It is further noted that, while the spiral torsion spring 62 has been described as spinning the sample container, it is noted that such a spring, or another type of spring, can provide for mixing in other ways.

Figure 7:
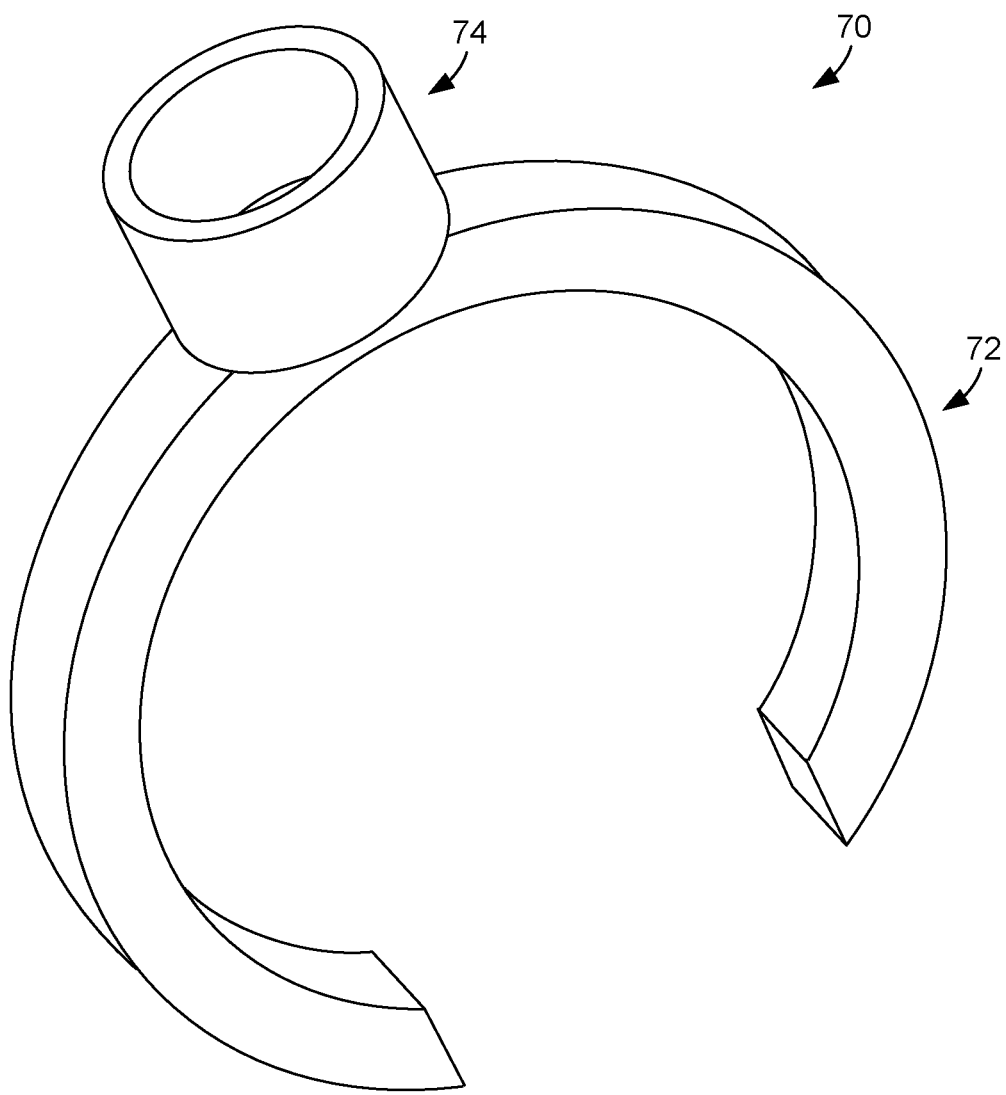
FIG. 7 is a perspective view of fourth embodiment of a mixing device configured to mix drawn blood collected in a sample container.

FIG. 7 illustrates another embodiment of a mixing device 70. In this embodiment, the mixing device 70 comprises a ring 72 that can be worn around one or more of the medical practitioner's fingers. Provided on the ring 72 is a housing 74 that is configured to support a mixing element, such as a vibration motor. An activation switch (not shown) can be provided on the ring 72 or the housing 74 so that, when the sample container 22 is grasped by a medical practitioner wearing the ring, the container presses the switch to automatically activate the mixing element.

It is noted that various features can be added to any of the above-described mixing devices. For example, heating and/ or cooling elements can be added to the mixing device. In some embodiments, heating can be provided with an integral electrical heating element. Heating and/or cooling can be supplied by providing a heating and/or cooling medium (e.g., a gel medium) within the mixing device that maintains a relatively high temperature or relatively low temperature, depending upon the environment in which the mixing device is stored (e.g., a warming chamber or refrigerator). In other embodiments, heating and/or cooling can be provided by an additional member that is configured to receive the mixing device.

The invention claimed is:

1. An integrated device comprising:
    a sample container configured to collect a liquid sample through an opening of the container;
    a cap configured to seal the opening of the sample container;
    a sleeve that surrounds at least a part of the sample container;
    a housing associated with the sleeve;
    a mixing element contained within the housing that is configured to mix the liquid sample contained within the sample container; and
    an activation element configured to automatically activate the mixing element when the cap is removed from the sample container.

2. The integrated device of claim 1, wherein the sleeve includes a slot that extends along the length of the sleeve.

3. The integrated device of claim 1, wherein the mixing element is a vibration motor.

4. The integrated device of claim 1, wherein the mixing element is a rotary motor configured to spin the sample container.

5. The integrated device of claim 1, further comprising a central controller contained within the housing that controls operation of the device.

* * * * *